(12) United States Patent
Ward et al.

(10) Patent No.: US 7,015,035 B2
(45) Date of Patent: Mar. 21, 2006

(54) RD114-BASED RETROVIRAL PACKAGING CELL LINE AND RELATED COMPOSITIONS AND METHODS

(75) Inventors: Maureen Ward, New York, NY (US); Arthur Bank, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/702,761

(22) Filed: Nov. 5, 2003

(65) Prior Publication Data

US 2004/0203156 A1    Oct. 14, 2004

Related U.S. Application Data

(60) Provisional application No. 60/424,077, filed on Nov. 5, 2002.

(51) Int. Cl.
*C12N 5/00*     (2006.01)
*C12N 15/00*    (2006.01)
*A61K 39/21*    (2006.01)

(52) U.S. Cl. .................. 435/325; 435/69.1; 424/207.1; 536/23.1; 536/23.72

(58) Field of Classification Search ................ 435/325, 435/69.1; 424/207.1; 536/23.1, 23.72
See application file for complete search history.

(56) References Cited

U.S. PATENT DOCUMENTS 5,681,746 A * 10/1997 Bodner et al. ............... 435/350
5,952,225 A *  9/1999 Pensiero et al. ............ 435/352
6,372,502 B1    4/2002 Bank et al.

OTHER PUBLICATIONS

Ward et al. Establishment of a Stable RD114 Retroviral Packaging Cell Line that Efficiently Transduces Human Hematopeietic Progenitors, Blood, Nov. 16, 2001, vol. 98, No. 11, Part 2, pp. 408b.*

Burns J., et al. (1993) Vesticular stomatitius virus G glycoprotein pseudotyped retroviral vectors: Concentration to very high titer and efficient gene transfer into mammalian and non-mammalian cells. Proc. Natl. Acad. Sci. USA 90:8033-8037.

Cone, R.D. and Mulligan, R.C. (1984) High-efficiency gene transfer into mammalian cells: generation of helper-free recombinant retrovirus with broad mammalian host range. Proc. Natl. Acad. Sci. USA 81:6349-6353.

Cosset F.L., et al., (1995) High-titer packaging cells producing recombinant retroviruses resistant to human serum. J. Virology 69:7430-7436.

Gatlin J., et al. (2001) Engraftment of NOD/SCID Mice with human CD34+ Cells transduced by concentrated oncoretroviral vector particles pseudotyped with the feline endogenous retrovirus (RD114) Envelope Protein. J. Virology 75:9995-9999.

Gerin et al. (1999) Improved titers of retroviral vectors from the human FLYRD18 packaging cell line in serum-and protein-free medium. Human Gene Ther. 10:1965-1974.

Kaubisch A., et al. (1999) Up-regulation of amphotrophic receptor expression in human peripheral blood CD34+ cells. Am. J. Hematol. 61:243-253.

Kavanaugh M.P., et al. (1994) Cell-surface receptors for gibbon ape leukemia virus and amphotrophic murine retrovirus and inducible sodium-dependent phosphate symporters. Proc. Natl. Acad. Sci. USA 91:7071-7075.

Kelly, P.F., et al. (2000) Highly efficient gene transfer into cord blood nonobese diabetic/severe combined immunodeficiency repopulating cells by oncoretroviral vector particles pseudotyped with the feline endogenous retrovirus (RD114) envelope protein. Blood 96:1206-1214.

Markowitz, et al. (1988) A safe packaging line for gene transfer: separating viral genes on two different plasmids, J. Virology 62:1120-1124.

Markowitz D., et al. (1988) Construction and use of a safe and efficient amphotropic packaging cell line. Virology 167:400-406.

Miller, A.D. and Buttimore, C. (1986) Redesign of retrovirus packaging cell lines to avoid recombination leading to helper virus production. Mol. Cell. Biol. 6:2895-2902.

Orlic D., et al. (1996) The level of mRNA encoding the amphotropic retrovirus receptor in mouse and human hermatopoietic stem cells is low and correlates with the efficiency of retrovirus transduction. Proc. Natl. Acad. Sci. USA 93:11097-11102.

Pensiero M. N., et al. (1996) Development of Amphotropic Murine Retrovirus Vectors Resistant to Inactivation by Human Serum. Human Gene Therapy 7:1095-1101.

Porter C. D., et al. (1996) Comparison of Efficiency of Infection of Human Gene Therapy Target Cells via Different Retroviral Receptors. Human Gene Therapy 7:913-919.

(Continued)

*Primary Examiner*—Stacy B. Chen
(74) *Attorney, Agent, or Firm*—John P. White, Esq.; Cooper & Dunham LLP

(57) ABSTRACT

This invention provides a retroviral packaging cell comprising a suitable mammalian cell having therein (i) a first recombinant nucleic acid comprising MMLV gag and pol genes and a selectable marker, and (ii) a second recombinant nucleic acid comprising RD114 envelope gene and a selectable marker, wherein the MMLV gag and pol genes and the RD114 envelope gene are stably expressed in the cell. This invention further provides related production methods, virions and kits.

10 Claims, 4 Drawing Sheets

OTHER PUBLICATIONS

Raftopoulos H., et al. (1997) Long-Term Transfer and Expression of the Human β-Globin Gene in a Mouse Transplant Model. Blood 90(9):3414-3422.

Sorge, J., et al. (1984) Amphotropic retrovirus vector system for human cell gene transfer. Mol. Cell. Biol. 4:1730-1737.

Takeuchi, Y., et al. (1994) Type C retrovirus inactivation by human complement is determined by both the viral genome and the producer cell. J. Virology 68:8001-8007.

Ward M., et al. (1994) Transfer and Expression of the Multiple Drug Resistance Gene in Human CD34 Cells. Blood 84(5):1408-1414.

Ward M., et al. (1996) Retroviral Transfer and Expression of the Human Multiple Drug Resistance (*MDR*) Gene in Peripheral Blood Progenitor Cells. Clinical Cancer Research 2:873-876.

* cited by examiner

RD114-BASED RETROVIRAL PACKAGING CELL LINE AND RELATED COMPOSITIONS AND METHODS

This application claims the benefit of U.S. Provisional Application No. 60/424,077, filed Nov. 5, 2002, the contents of which are hereby incorporated by reference.

This invention was made with funding from the United States National Institute of Health, Grant No. 1-RO1-HL-59887-05. Accordingly, the United States Government has certain rights in this invention.

Throughout this application, various publications are referenced. Full bibliographic citations for these publications are found at the end of the specification immediately preceding the claims. The disclosures of these publications in their entirety are hereby incorporated by reference into this application.

BACKGROUND OF THE INVENTION

Retroviral Vectors and Retroviral Packaging Cell Lines

A retrovirus is an RNA viral molecule encapsulated in a viral protein envelope which infects a host cell, reverse transcribes its RNA molecule into DNA, and integrates its genome stably into the host cell's genome. Systems for packaging retroviral vectors into viral particles to form virions have been developed to facilitate the transfer of exogenous genes into target cells for the purpose of gene therapy. A retroviral vector is DNA or RNA that has been modified to serve as a vector for recombinant DNA. Retroviral vectors can transfer genes into a wide variety of cell types from many different species.

The retroviral particles required to carry out retroviral-mediated gene transfer are produced by packaging cells. Packaging cell lines synthesize all retroviral proteins required for assembly of non-self-replicating infectious retrovirus, and are designed so as to not produce any replication-competent virus. Packaging cells become producer cells when they are transfected with a retroviral vector carrying the gene of interest. Producer cells "package" a retroviral vector into viral particles, thereby producing virions which can be used to transfer the gene of interest to target cells.

The three retroviral genes required to make functional viral particles are (i) gag (encoding internal structure proteins); (ii) pol (encoding RNA dependent DNA polymerase, and protease and integrase proteins); and (iii) env (encoding viral envelope protein). In addition to these three genes, a wild-type retroviral genome usually contains two long terminal repeat sequences (LTRs) and a packaging sequence Ψ sequence). The two LTRs, one located at the 5' end and the other at the 3' end of the viral nucleic acid, are necessary for reverse transcription of the viral RNA sequence into DNA and stable integration of the viral genome into the host cell's DNA. The Ψ sequence is required for packaging of viral RNA into the viral particles. Without a nucleic acid sequence containing a Ψ sequence, cells expressing the viral genes gag, pol and env will only produce empty viral particles.

A safety feature of self-replication-deficient retroviral packaging cell lines is that the viral genes required for producing viral particles are placed onto two separate plasmids, with the gag and pol sequences on one plasmid and env sequence on another. Neither plasmid contains the Ψ sequence or a 3' LTR. When packaging cells are transfected with a viral vector comprising the gene to be transferred, a Ψ sequence and a 3' LTR, virions carrying the gene of interest are produced. In this system, infectious self-replicating wild-type virus can only be produced if three separate and highly improbable recombination events result in all the required viral genomic sequences (i.e., gag, pol, env and Ψ sequence) coming together in one element.

Packaging cells can express the viral gag, pol and env genes either transiently from separate unintegrated plasmids or stably from these viral genes which have been integrated into the packaging cell's genome. Stable packaging cell lines are advantageous because they can reliably produce the large quantities of virions required for effective retroviral-mediated gene therapy protocols (Bank et al., U.S. Pat. No. 6,372,502 and Markowitz, 1988b).

Challenges to Effective Retroviral-Mediated Gene Therapy

Some cell types are not efficiently transduced by viral particles produced by currently available packaging cells. In order for a viral particle to enter a target cell, the target cell must express a receptor which recognizes the viral envelope protein. Amphotropic retroviruses can infect a wide range of cell types, and therefore, packaging cells expressing amphotropic retroviral genes have been developed and are commonly used (Cone, 1984; Miller, 1986; and Sorge, 1984).

Hematopoietic stem cells (HSCs) are an important target cell type for gene therapy. This cell type can be readily isolated from a patient, transduced ex vivo with a retroviral vector containing the therapeutic gene and then reintroduced into the patient.

One stable retroviral packaging system currently used to produce virions for transducing human hematopoietic stem and progenitors cells expresses the Moloney Leukemia Virus (MLV) gag and pol genes and the GLVR-1 or GLVR-2 viral envelope gene. The GLVR-1 and GLVR-2 retroviral envelope proteins are known to target amphotropic receptors (Markowitz, 1988b; Ward, 1994; and Ward, 1996). Viral particles produced by this type of stable amphotropic packaging system have poor transduction efficiency of HSCs because these target cells express low levels of amphotropic envelope protein receptors on their cell membranes (Orlic, 1996; Kaubisch, 1999; and Kavanaugh, 1994). In addition, amphotropic stable packaging cell lines generally are unable to produce the requisite titer ($10^6$ or greater viral particles per ml) necessary to compensate for the low levels of receptor expression on HSCs. Researchers have reported that amphotropic viruses pseudotyped with other viral envelopes, such as the vesticular stomatitis G protein (VSV-G), can improve transduction efficiency. The VSV-G envelope protein enables effective targeting of a variety of cells, including HSCs. Higher viral titers can be achieved using VSV-G envelope protein pseudotyped viral particles because these viral particle supernatants can be concentrated by ultracentrifugation (Burns, 1993). One limitation of this system is that expression of the VSV-G protein is toxic to the packaging cells. Consequently, only transient or inducible packaging lines are feasible using this viral envelope protein.

An alternative to the VSV-G envelope protein is the feline endogenous virus envelope (RD114). RD114 pseudotyped viral particles are able to efficiently target human HSCs and can be concentrated by ultracentrifugation (Porter, 1996; and Gatlin, 2001). A RD114 pseudotyped virion has been shown to transfer the green fluorescent protein (GFP) gene into human HSCs at high levels (Kelly, 2000). Virions used in this study were produced by a transient retroviral packaging system in which unintegrated expression plasmids for gag and pol genes, and the RD114 envelope protein gene were transiently transfected into 293T cells (derived from human embryonic kidney cells) Transient packaging systems, however, can not produce the large quantities of virions required for human clinical trials.

The FLYRD18 packaging cell line is a stable packaging cell line that produces RD114 pseudotyped virions. However, the use of this cell line for producing virions for transducing HSCs is limited because the viral supernatant produced by these packaging cells causes phenotypic changes and loss of primitive repopulating cells (Kelly, 2000).

For successful transduction of HSCs and other target cell types for gene therapy in humans, a viral packaging cell line must (i) produce large quantities of retroviral particle supernatants; (ii) produce viral particles that efficiently transduce the target cell; and (iii) only produce replication-defective viral particles. To date, there remains a need for such cell lines.

SUMMARY OF THE INVENTION

This invention provides a first retroviral packaging cell comprising a suitable mammalian cell having therein (i) a first recombinant nucleic acid comprising MMLV gag and pol genes and a selectable marker, and (ii) a second recombinant nucleic acid comprising RD114 envelope gene and a selectable marker, wherein the MMLV gag and pol genes and the RD114 envelope gene are stably expressed in the cell.

This invention further provides a second retroviral packaging cell designated RDF 21 (ATCC Patent Deposit Designation PTA-4440).

This invention further provides a first method for producing a retroviral packaging cell comprising (a) transfecting a plurality of suitable mammalian cells with a recombinant nucleic acid comprising RD114 envelope gene and a selectable marker, each mammalian cell having therein a recombinant nucleic acid comprising MMLV gag and pol genes, which gag and pol genes are stably expressed in the cell; and (b) isolating from among the resulting transfected cells of step (a) a cell which stably expresses the RD114 envelope gene, thereby producing a retroviral packaging cell.

This invention further provides a second method for producing a retroviral packaging cell comprising (a) transfecting a plurality of suitable mammalian cells with (i) a first recombinant nucleic acid comprising the MMLV gag and pol genes and a selectable marker, and (ii) a second recombinant nucleic acid comprising RD114 envelope gene and a selectable marker; and (b) isolating from among the resulting transfected cells of step (a) a cell which stably expresses the gag, pol and RD114 genes, thereby producing a retroviral packaging cell.

This invention further provides a first method for producing a retroviral producer cell comprising transducing the first retroviral packaging cell with a retroviral vector comprising a nucleic acid sequence of interest so as to cause the cell to secrete virions comprising the nucleic acid sequence of interest, thereby producing a retroviral producer cell.

This invention further provides a second method for producing a retroviral producer cell comprising transducing the second retroviral packaging cell with a retroviral vector comprising a nucleic acid sequence of interest so as to cause the cell to secrete virions comprising the nucleic acid sequence of interest, thereby producing a retroviral producer cell.

This invention further provides a first retroviral producer cell produced by the first method for producing a retroviral producer cell.

This invention further provides a first method for producing high-titer retroviral supernatant comprising culturing the first retroviral producer cell under suitable conditions, thereby producing high-titer retroviral supernatant.

This invention further provides a second retroviral producer cell produced by the second method for producing a retroviral producer cell.

This invention further provides a second method for producing high-titer retroviral supernatant comprising culturing the second retroviral producer cell under suitable conditions, thereby producing high-titer retroviral supernatant.

This invention further provides a virion produced by the first retroviral producer cell.

This invention further provides a virion produced by the second retroviral producer cell.

This invention further provides a kit comprising the first retroviral packaging cell, and instructions for use.

This invention further provides a kit comprising the first retroviral packaging cell and a retroviral vector comprising a nucleic acid of interest.

This invention further provides a kit comprising the second retroviral packaging cell and instructions for use.

Finally, this invention further provides a kit comprising the second retroviral packaging cell and a retroviral vector comprising a nucleic acid of interest.

Each group of bars represents one experiment. The experiment number and the multiplicity of infection (MOI, virus to cell ratio) are listed below each grouping.

Figure 4:
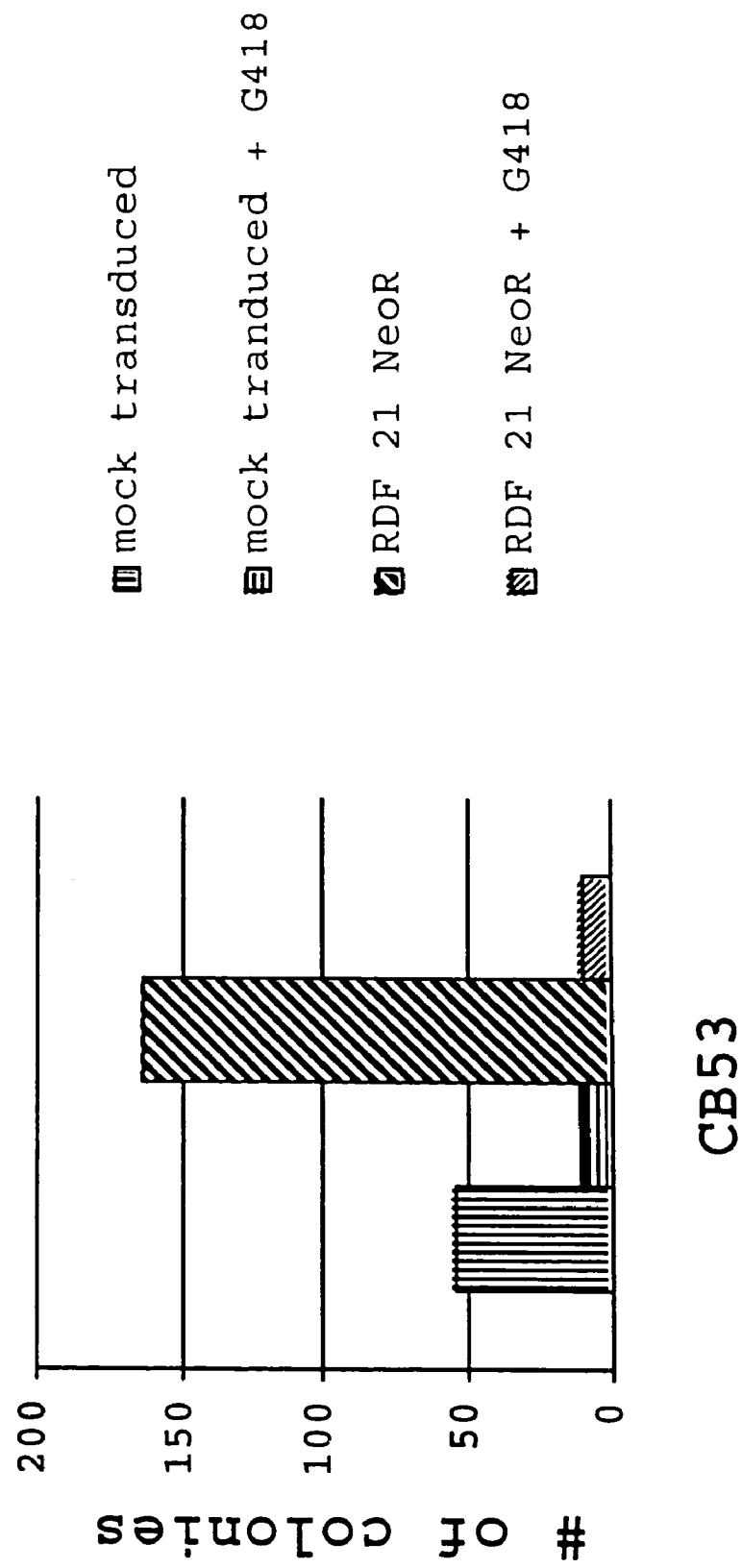

FIG. 4 Number of G418-resistant progenitor colonies from CD34+ cells (cord blood sample 53) transduced with unconcentrated RDF 21 Neo$^R$ virus. The multiplicity of infection (MOI, virus to cell ratio) was 3 to 1.

DETAILED DESCRIPTION OF THE INVENTION

This invention provides a first retroviral packaging cell comprising a suitable mammalian cell having therein (i) a first recombinant nucleic acid comprising MMLV gag and pol genes and a selectable marker, and (ii) a second recombinant nucleic acid comprising RD114 envelope gene and a selectable marker, wherein the MMLV gag and pol genes and the RD114 envelope gene are stably expressed in the cell. In one embodiment, the suitable mammalian cell is a human 293 cell. In the preferred embodiment, the suitable mammalian cell is a mouse 3T3 cell. In one embodiment, each of the first and second nucleic acids is DNA.

As used herein, a "packaging cell" is a mammalian cell capable of expressing retroviral genes and assembling retroviral particles. "Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996–1997, Roche Molecular Systems, Inc., Branchburg, N.J., USA).

The vectors encoding the retroviral RD114 envelope protein, the retroviral Gag and Pol proteins, and the vector comprising a heterologous gene of interest can be integrated in a chromosome of the packaging cell.

Cells suitable for use in preparing the packaging cell lines of the present invention are derived from vertebrates and include, but are not limited to, primate, porcine, human, murine, and canine-derived cells. However, other suitable cells can be used.

This invention further provides a second retroviral packaging cell designated RDF 21 (ATCC Patent Deposit Designation PTA-4440).

This invention provides a first method for producing a retroviral packaging cell comprising (a) transfecting a plurality of suitable mammalian cells with a recombinant nucleic acid comprising RD114 envelope gene and a selectable marker, each mammalian cell having therein a recombinant nucleic acid comprising MMLV gag and pol genes, which gag and pol genes are stably expressed in the cell; and (b) isolating from among the resulting transfected cells of step (a) a cell which stably expresses the RD114 envelope gene, thereby producing a retroviral packaging cell. In the preferred embodiment, the suitable mammalian cell is a GP101 cell.

This invention further provides a second method for producing a retroviral packaging cell comprising (a) transfecting a plurality of suitable mammalian cells with (i) a first recombinant nucleic acid comprising the MMLV gag and pol genes and a selectable marker, and (ii) a second recombinant nucleic acid comprising RD114 envelope gene and a selectable marker; and (b) isolating from among the resulting transfected cells of step (a) a cell which stably expresses the gag, pol and RD114 genes, thereby producing a retroviral packaging cell. In one embodiment, the suitable mammalian cell is a human 293 cell. In the preferred embodiment, the suitable mammalian cell is a mouse 3T3 cell.

This invention further provides a first method for producing a retroviral producer cell comprising transducing the first retroviral packaging cell with a retroviral vector comprising a nucleic acid sequence of interest so as to cause the cell to secrete virions comprising the nucleic acid sequence of interest, thereby producing a retroviral producer cell.

Representative nucleic acid sequences of interest in the present invention can encode, for example, (i) a replacement or substitute gene for a defective or missing enzyme or other protein, (ii) an RNA molecule or ribozyme, or (iii) a therapeutic protein or RNA molecule normally not present in the cell. Examples of nucleic acids of interest include, but are not limited to, those which encode β-globin, blood clotting factors, receptors, cystic fibrosis transmembrane conductance regulator (CFTR), tumor suppressors, antisense RNAs, and vaccine antigens.

This invention further provides a second method for producing a retroviral producer cell comprising transducing the second retroviral packaging cell with a retroviral vector comprising a nucleic acid sequence of interest so as to cause the cell to secrete virions comprising the nucleic acid sequence of interest, thereby producing a retroviral producer cell.

In one embodiment of these methods, the retroviral vector is a MMLV vector. In another embodiment of these methods, the retroviral vector is a lentiviral vector. In yet another embodiment of these methods, the nucleic acid of interest comprises a therapeutic gene. In still a further embodiment of these methods, the nucleic acid of interest further comprises a selectable marker.

Selectable markers include, for example, (i) the neomycin and hygromycin phosphotransferase genes that confer resistance to G418 and hygromycin, respectively; (ii) the mutant mouse dihydrofolate reductase gene (dhfr*) which confers resistance to methotrexate; (iii) the bacterial gpt gene which allows cells to grow in medium containing mycophenolic acid, xanthine, and aminopterin; (iv) the bacterial hisD gene which allows cells to grow in medium without histidine but containing histidinol; and (v) the multidrug resistant gene (mdr) which confers resistance to a variety of drugs. These markers are dominant selectable markers and allow chemical selection of most cells expressing these genes.

This invention also provides a first retroviral producer cell produced by the first method for producing a retroviral producer cell.

This invention further provides a first method for producing high-titer retroviral supernatant comprising culturing the first retroviral producer cell under suitable conditions, thereby producing high-titer retroviral supernatant. In one embodiment, the method further comprises the steps of collecting and concentrating the retroviral supernatant.

This invention further provides a second retroviral producer cell produced by the second method for producing a retroviral producer cell.

This invention still further provides a second method for producing high-titer retroviral supernatant comprising culturing the second retroviral producer cell under suitable conditions, thereby producing high-titer retroviral supernatant. In one embodiment, the method further comprises the steps of collecting and concentrating the retroviral supernatant.

This invention also provides a virion produced by the first retroviral producer cell.

This invention further provides a virion produced by the second retroviral producer cell.

This invention provides a kit comprising the first retroviral packaging cell, and instructions for use.

This invention also provides a kit comprising the first retroviral packaging cell and a retroviral vector comprising a nucleic acid of interest. In one embodiment, the kit further comprises instructions for use.

This invention further provides a kit comprising the second retroviral packaging cell and instructions for use.

Finally, this invention further provides a kit comprising the second retroviral packaging cell and a retroviral vector comprising a nucleic acid of interest. In one embodiment, the kit further comprises instructions for use.

This invention is illustrated in the Experimental Details section which follows. This section is set forth to aid in an understanding of the invention but is not intended to, and should not be construed to limit in any way, the invention as set forth in the claims which follow thereafter.

Experimental Details

A. Methods and Materials

RDF 21 Packaging Cell Line

Figure 1A:
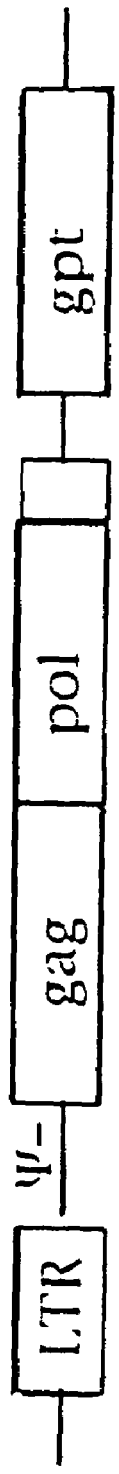
FIG. 1 Retroviral constructs used to make RD114 stable packaging line. (a) Vector expressing the Moloney Leukemia Virus gag and pol genes. (b) Vector expressing the RD114 feline endogenous viral envelope gene. (c) Self-inactivating retroviral vector expressing the Neo$^R$ gene with a PGK promoter.
Figure 1B:
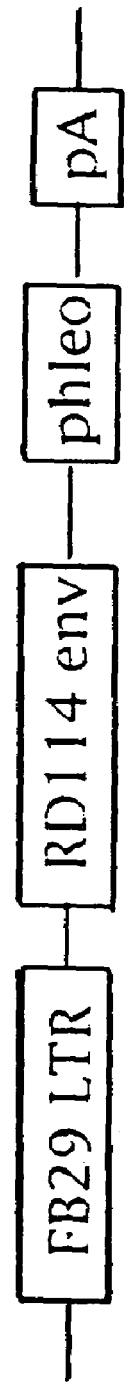
Figure 1C:
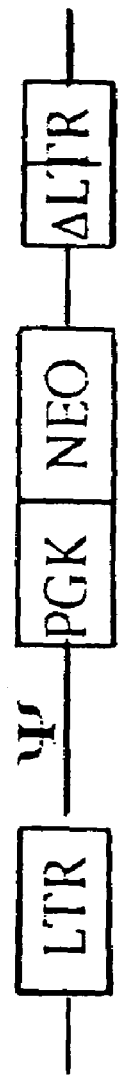

Cell culture. The GP101 cell line is a mouse 3T3 cell line stably transfected with a plasmid containing both the gag and pol genes from the Moloney Leukemia virus (MMLV) and the gpt selectable marker (Markowitz, 1988b). The vector expressing the gag and pol proteins from the Moloney Leukemia virus (MMLV) is depicted in FIG. 1, Panel a. All cells were grown in Dulbecco's modified Eagle's media (DME, Life Technologies) and 10% newborn calf serum.

HeLa cells were grown in DME and 10% fetal calf serum. All cells were grown at 37° C. and 5% $CO_2$.

Expression plasmid/retroviral vector. RDF is an expression plasmid/retroviral vector containing the RD114 env gene and a selectable marker, the phleomycin resistance gene, regulated by a FB29 Friend MLV LTR promoter (FIG. 1, Panel b)(Cosset, 1995).

The SIN-PGK Neo plasmid retroviral vector ($Neo^R$) used in these experiments is a Moloney leukemia viral vector with the self-inactivating or SIN deletion and the neomycin gene regulated by a PGK promoter. This vector was made by deleting the β-globin gene from the p141 vector described elsewhere (FIG. 1, Panel c)(Raftopoulos, 1997).

Transfection of GP101 and selection for RD114 stable packaging clones. $2\times10^6$ GP101 cells were transfected with 10 μg of RDF plasmid using Lipofectin® 2000 from Life Technologies following manufacturer's recommendations. Cells were selected with 6 μg/ml phleomycin in four 24-well plates for 20 days. Individual clones were trypsinized, replated, and expanded for analysis.

Analysis of RD114 stable packaging clones. RNA was made from RD114 stable packaging clones using Trizol reagent from Life Technologies following manufacturer's instructions. 5 μg of RNA was run on a 1.2% agarose gel and blotted by standard procedures. Blots were probed with a [$^{32}$P]-labeled 1 kb probe made by PCR amplification of the RDF plasmid, washed, and exposed to film. Band density was quantitated by Imagequant® software. The blot was stripped and reprobed using a G3PDH cDNA control probe from Clontech. Clones expressing high levels of RD114 env mRNA were selected for further testing.

RDF 21 $Neo^R$ Producer Clone

Transfection of RD114 stable packaging clone with a retroviral vector. RD114 packaging clone 21 (RDF 21) was transfected by calcium phosphate precipitation with 10 μg of SIN-PGK Neo plasmid ($Neo^R$ retroviral vector) (FIG. 1, Panel c). Cells were selected in media containing 800 μg of G418 for 10 days and individual clones were trypsinized, replated, and expanded for analysis.

Viral supernatant production and concentration. The highest titer ($1\times10^5$ virus/ml) RDF 21 $Neo^R$ producer clone was isolated. This producer clone was used to make concentrated viral supernatants. RDF 21 $Neo^R$ viral producer cells were grown in 100 mm dishes in DME, 10% FCS until semi-confluent. Cells were fed fresh media the day before harvesting virus. Supernatants from plates were removed, pooled, and filtered through a 45μ filter unit. Virus was concentrated by spinning at 23K in a SW41 rotor for 90 minutes. Viral pellets were resuspended overnight in media, pooled and kept frozen at −80° C. These concentrated supernatants were used to transduce cord blood CD34+ cells (see below).

Titering of viral supernatants. Viral titers of RDF 21 $Neo^R$ retroviral supernatants were determined by counting G418-resistant Hela cell colonies. $2\times10^5$ Hela cells were plated in a 60 mm dish and exposed to dilutions of viral supernatant supplemented with 10 μg/ml polybrene. 24 hours later Hela cells were selected with 800 μg/ml G418. Twelve to 14 days after selection, clones were counted and viral titers calculated by multiplying the number of colonies by the viral dilution.

Transduction of Target Cells

Isolation of human CD34+ cells from cord blood. 90 to 180 ml samples of cord blood were obtained from recent (within 24 hours) births. Samples were diluted with phosphate buffered saline (PBS) and mononuclear cells (MNC) were ficoll density gradient separated. CD34+-enriched populations were isolated by negative selection using a lineage negative selection cocktail from Stem Cell Technologies (Vancouver, CA). The CD34+-enriched population was qualified by FACS analysis for % CD34+-cells and for progenitor enrichment by plating in methylcellulose media containing colony stimulating growth factors (Stem Cell Technologies, Vancouver, BC).

Transduction of human CD34+ cells. The CD34+-enriched population was cultured for 24 to 48 hours on Retronection-coated plates, in Iscove's modified Dulbecco's media (IMDM) supplemented with 20% BIT serum substitute from Stem Cell Technologies, as well as growth factors: stem cell factor (SCF), thrombopoeitin (TPO), interleukin 6 (IL6), flt3 ligand, and granulocyte colony-stimulating factor (G-CSF). After 24 to 48 hours, an aliquot of concentrated RDF 21 $Neo^R$ virus was added to the cells and left overnight. Mock transduced cells were given the same volume of media without virus. Cells were collected and counted the following day. $1\times10^3$ cells were plated in methylcellulose (Stem Cell Technologies) with or without 1 mg/ml G418 and colonies were scored 14 days later.

Colonies were also analyzed by PCR for the presence of the $Neo^R$ gene using specific primers as described previously (Raftopoulos, 1997). Colonies were picked by mouth pipetting, washed in phosphate buffered saline, and resuspended in 200 μl of InstaGene™ Matrix (BioRad, Hercules, Calif.). Samples were incubated at 55° C. for 30 minutes and then boiled for 5 minutes. The matrix was pelleted and 25 μl of the aqueous sample was amplified by PCR as described (Raftopoulos, 1997).

B. Results

RD114 Expression in Stable Retroviral Packaging Clones

Fifteen RD114 packaging clones were analyzed by Northern blot to quantitate the level of RD114 transcript (Table 1). Two bands were seen at approximately 2.9 kb and were determined to be the RNA expression products of the RDF plasmid. No bands were seen in the GP101 control RNA lane. All clones including the GP101 control had a 1.4 kb band when probed with the G3PDH probe. Two clones, 21 and 22, had very high RD114 envelope expression when normalized to G3PDH expression. In the experiments to follow, RD114 clone 21 (RDF 21) was used as the packaging cell and this clone is the clone specified in the subject application, although other useful clones may be isolated using the procedure described above.

TABLE 1

Analysis of RD114 packaging clones

| CLONE DESIGNATION | NORMALIZED RD114 RNA LEVELS |
|---|---|
| Clone 1 | 0.33 |
| Clone 3 | 0.34 |
| Clone 6 | 0.49 |
| Clone 7 | 0.70 |
| Clone 10 | 1.65 |
| Clone 13 | 1.94 |
| Clone 15 | 0.40 |
| Clone 16 | 1.80 |
| Clone 17 | 3.40 |
| Clone 18 | 2.30 |
| Clone 21 | 8.90 |
| Clone 22 | 12.10 |
| Clone 23 | 0.46 |
| Clone 25 | 1.18 |
| Clone 26 | 0.70 |
| Negative Control-GP101 | 0.40 |

Reproducibility of the RDF 21 Packaging Cell Line

The RDF 21 cell line has been cultured and passaged continuously for over a year without any decrease in the efficacy of the viral particles produced.

The packaging cell line RDF 21 was deposited with the American Type Culture Collection, 10801 University Boulevard, Manassas, Va. 20110-2209, Jun. 5, 2002, under the conditions of the Budapest Treaty and has been assigned the Patent Deposit Designation PTA-4440.

Titer Results

Figure 2:
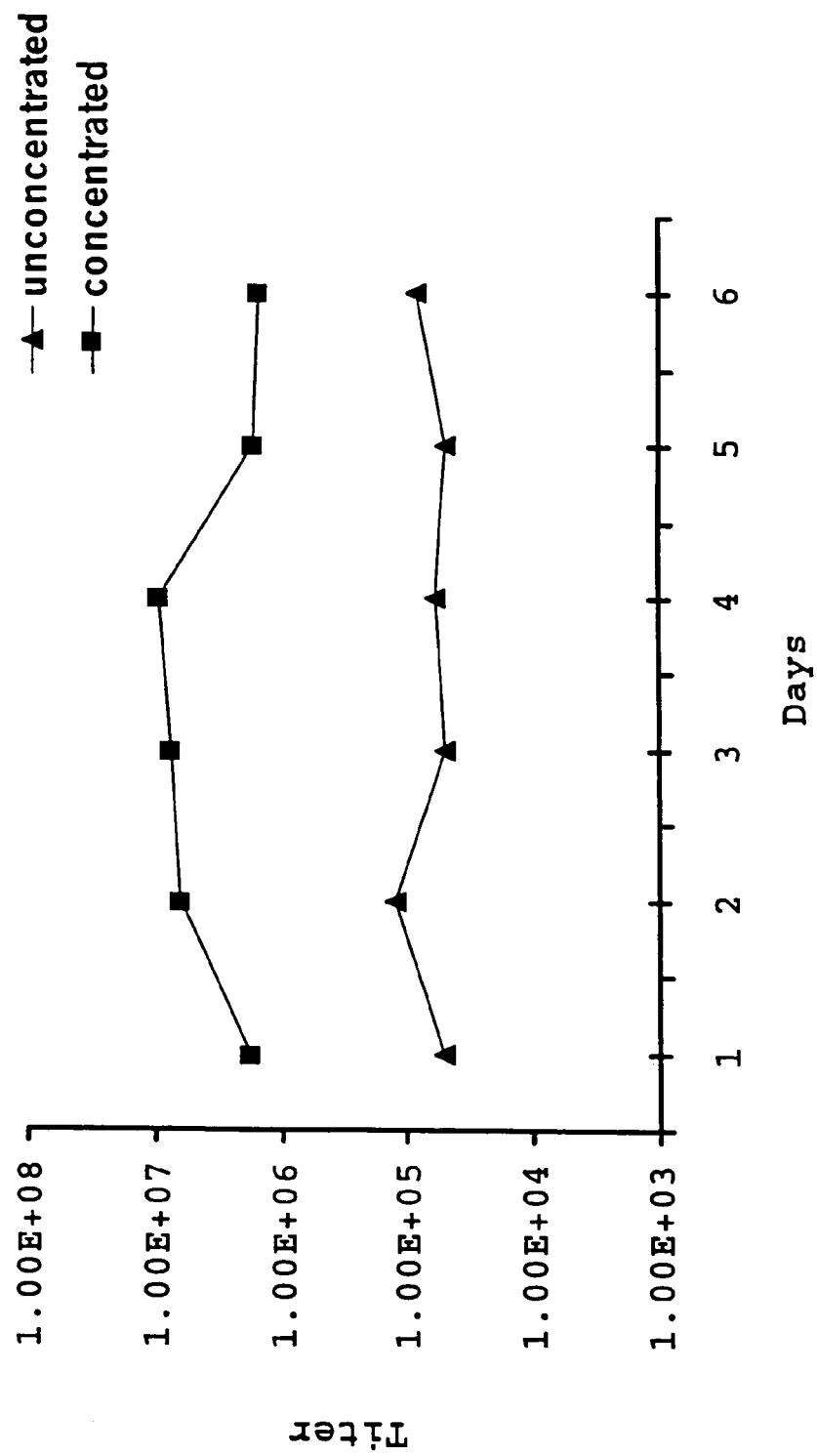
FIG. 2 Production and concentration of RD114 pseudotyped viral particles from a stable viral producer (RDF 21 Neo$^R$) over a six day harvest period. Diamonds represent unconcentrated viral titers as determined on Hela cells and squares represent titers of concentrated viral supernatants.

Using ultracentrifugation, RDF 21 $Neo^R$ viral supernatants were concentrated by approximately 1.5 logs, increasing the titer from $5-10 \times 10^4$ to $1-10 \times 10^6$ (Table 2 and FIG. 2). The RDF 21 $Neo^R$ producer cultures stably produced high titer virus over a six day period.

TABLE 2

Summary of viral titers pre and post concentration

| Day | Concentrated Titer (virus/ml) | Unconcentrated Titer (virus/ml) |
| --- | --- | --- |
| 1 | $1.80 \times 10^6$ | $5.00 \times 10^4$ |
| 2 | $6.50 \times 10^6$ | $1.30 \times 10^5$ |
| 3 | $8.00 \times 10^6$ | $5.00 \times 10^5$ |
| 4 | $1.00 \times 10^7$ | $6.00 \times 10^4$ |
| 5 | $1.80 \times 10^6$ | $5.00 \times 10^5$ |
| 6 | $1.60 \times 10^6$ | $9.00 \times 10^4$ |

Isolation of Human CD34+ Cells

Human cord blood was used as the source of CD34+ cells. Using the StemSep® negative selection system, cord blood samples were enriched to 46–62% CD34+ (Table 3). The progenitor colony potential (number of colonies per cells plated) was increased by 50 to 176-fold upon negative selection for CD34+ cells (Table 3), indicating that the mononuclear cell (MNC) population had been enriched for a progenitor population which contains HSCs.

Transduction of Human CD34+ Cells

Figure 3:
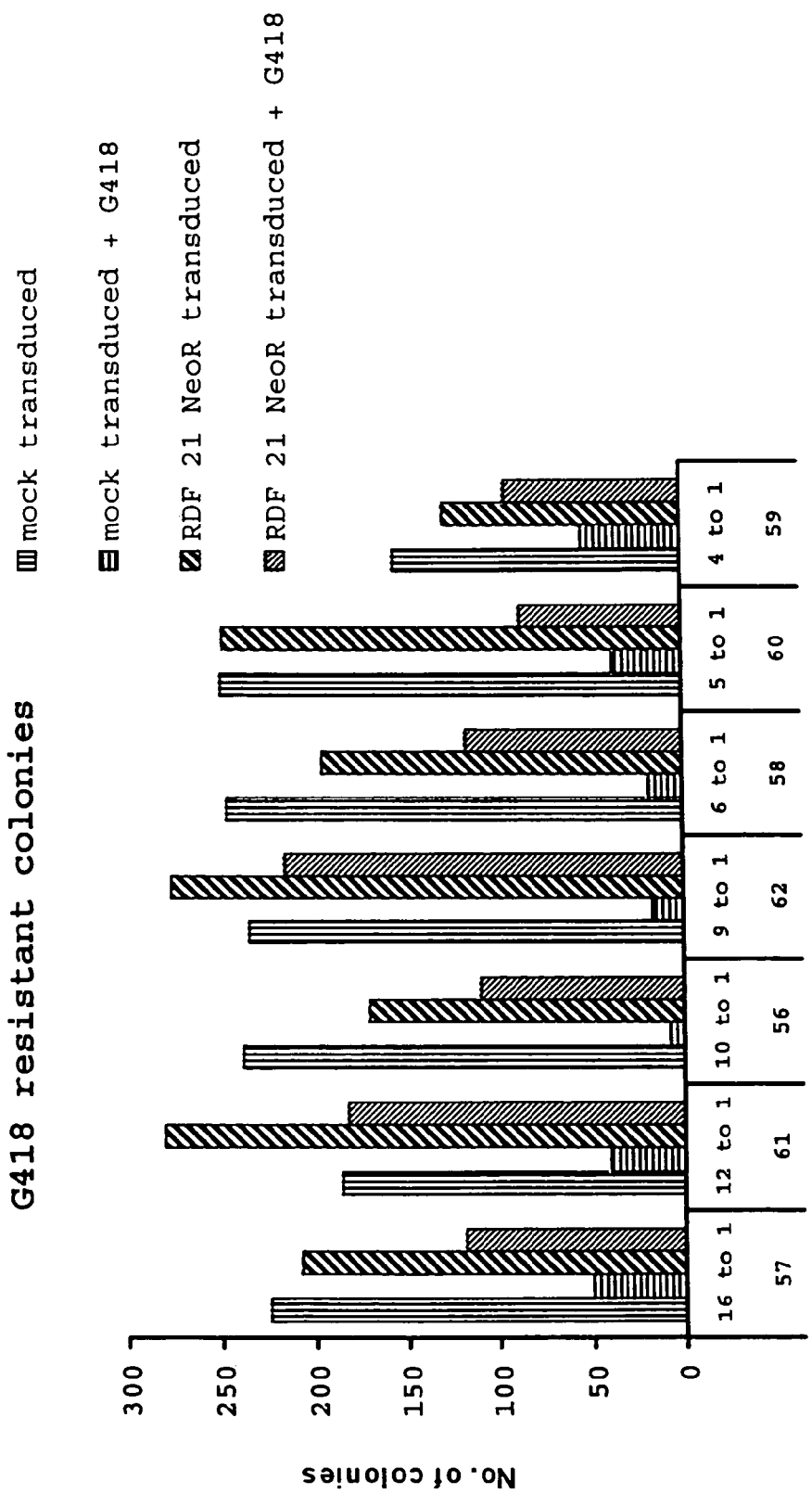
FIG. 3 Number of G418-resistant progenitor colonies from cord blood CD34+ cells transduced with concentrated RDF 21 Neo$^R$ virus.

Half of each sample of CD34+ cells was transduced as described at varying multiplicities of infection (MOI) using the concentrated RDF 21 $Neo^R$ virus and the other half of the sample was mock transduced by adding just media alone. 24 hours after the transduction, aliquots were plated in methylcellulose with or without 1 mg/ml G418 and the number of colonies scored after 14 days. FIG. 3 depicts the number of colonies that grew with or without G418 for each experiment. The number of progenitor colonies grown without G418 varied from sample to sample in the range of 100 to 250 colonies per $10^3$ cells. The number of G418-resistant colonies from transduced cells ranged from 35–78% of colonies grown without G418, with the average being around 62% (FIG. 3, Table 4). This level of transduction efficiency is greater than that achieved previously using unconcentrated RDF 21 $Neo^R$ supernatants (FIG. 4) in part because of the ability to deliver more virus to the cells in culture. However, the high density of viral particles may also play a role in increasing the efficiency of transduction. Some evidence for this is indicated by the fact that an increase in MOI from just 3:1 (FIG. 4) using unconcentrated virus to 4:1 or 5:1 (FIG. 3, experiments 59 and 60) using concentrated virus allows the growth of G418-resistant colonies where none were seen before. Due to the varying progenitor potential of each experimental sample, it is unclear if an increase in MOI has an effect on transduction efficiency. The transduction efficiency based on the number of G418-resistant colonies appears to be in the same range in all experiments regardless of MOI (Table 4). The $Neo^R$ PCR analysis of colonies grown without G418 closely reflects the G418 resistance data in 4 out of the 7 experiments (Table 4).

Transduction of CD34+ Cells Isolated from Sickle Cell Patients

A practical application of retoviral packaging cells is to produce virions carrying a retroviral vector with a therapeutically relevant gene. For example, the β-globin gene could be packaged into viral particles and used in gene therapy strategies for treating β-thalassemia and sickle cell disease.

The RDF 21 β-globin retroviral producer cell line (RDF 21 β-globin) was created by transfecting the RDF 21 packaging cell line with the p141 retroviral vector. The p141 retroviral vector contains the human β-globin gene as well as the $Neo^R$ gene and has been shown to work well in a mouse bone marrow transplant model (Raftopoulos, 1997). This producer cell line was used to make concentrated viral supernatants. Sickle exchange blood was obtained from patients undergoing apheresis treatment: CD34+ cells were isolated from these samples and transduced with the RDF 21 β-globin virions. Transduction efficiency of CD34+ cells by both RDF 21 β-globin virions and RDF 21 $Neo^R$ virions was 100% in G418-resistant progenitor clones (Table 5). PCR screening of progenitor clones from CD34+ colonies for the $Neo^R$ or β-globin genes, as appropriate, was used to measure transduction efficiency.

TABLE 3

Summary of CD34+ cell isolations from cord blood

| | | | CD34 enrichment | | # of methylcellulose colonies | |
| --- | --- | --- | --- | --- | --- | --- |
| Sample | Volume of blood (ml) | MNC* yield # of cells | # of cells | % CD34+ | MNC* (per $10^5$ cells) | CD34+ (per $10^3$ cells) |
| CB56 | 115 | $1.88 \times 10^8$ | $1.70 \times 10^6$ | 52% | 188 | 90 |
| CB57 | 150 | $6.10 \times 10^8$ | $2.77 \times 10^6$ | 46% | 152 | 138 |
| CB58 | 90 | $9.46 \times 10^8$ | $2.30 \times 10^6$ | 60% | 69 | 119 |
| CB59 | 145 | $6.01 \times 10^8$ | $3.00 \times 10^6$ | 62% | 163 | 203 |
| CB60 | 160 | $7.00 \times 10^8$ | $6.00 \times 10^6$ | 58% | 142 | 251 |
| CB61 (2 samples) | 180 | $6.30 \times 10^8$ | $6.35 \times 10^5$ | 47% | 84 | 144 |

TABLE 3-continued

Summary of CD34+ cell isolations from cord blood

| Sample | Volume of blood (ml) | MNC* yield # of cells) | CD34 enrichment | | # of methylcellulose colonies | |
|---|---|---|---|---|---|---|
| | | | # of cells | % CD34+ | MNC* (per $10^5$ cells) | CD34+ (per $10^3$ cells) |
| CB62 (2 samples) | 225 | $4.40 \times 10^9$ | $1.90 \times 10^6$ | 46% | 62 | 102 |

*MNC = mononuclear cells.

TABLE 4

Transduction efficiency of cord blood CD34$^+$ cells transduced with concentrated RDF 21 Neo$^R$ viral supernatants

| Experiment | MOI* | % G418 resistant colonies** | % Neo$^R$ PCR Positive colonies*** |
|---|---|---|---|
| 57 | 16 to 1 | 57% | 80% |
| 61 | 12 to 1 | 65% | 65% |
| 56 | 10 to 1 | 65% | 55% |
| 62 | 9 to 1 | 78% | 75% |
| 58 | 6 to 1 | 60% | 94% |
| 60 | 5 to 1 | 35% | 25% |
| 59 | 4 to 1 | 73% | 45% |

*Multiplicity of Infection; virus to cell ratio.
**Number of colonies grown in G418/number of colonies grown without G418.
***Number of Neo$^R$ PCR positive colonies/number of colonies PCR.

TABLE 5

Transduction efficiency of CD34$^+$ cells isolated from sickle cell patients transduced with concentrated RDF 21 Neo$^R$ or RDF 21 β-globin viral supernatants

| | MOI* | % PCR+ colonies (total positive/total tested) |
|---|---|---|
| RDF 21 Neo$^R$ | 5:1 | 44% (16/36) |
| RDF 21 Neo$^R$ + G418 | 5:1 | 100% (10/10) |
| RDF 21 β-globin | 5:1 | 0% (0/48) |
| RDF 21 β-globin + G418 | 5:1 | 100% (3/3) |
| Mock tranduced | — | 0% (0/10) |
| Mock transduced + G418 | — | 0% (0/10) |

*MOI = multiplicity of infection; virus to cell ratio.

C. Experimental Discussion

These studies show efficient gene transfer into human hematopoeitic progenitor cells using a concentrated RD114 pseudotyped virus (RDF 21 Neo$^R$). The increased concentration of the virus allows for a simpler and less invasive method of transduction.

The efficacy of the virions, produced by the RDF 21 cell line, in transducing CD34+ cells was surprising because previous studies have shown that mouse 3T3-derived packaging cell lines produce virions that are sensitive to human serum (Takeuchi, 1994 and Pensiero, 1996). Also, direct comparison of viral particles derived from a mouse NIH 3T3 packaging cell line performed poorly as compared to viral particles derived from a human HT1080 packaging cell line (Gerin, 1999). Contrary to expectations, viral particles produced by the NIH 3T3-derived RDF 21 packaging cell line exhibit superior transduction of human CD34+ cells as compared to currently available viral particles produced by other cell types.

This invention allows easier and safer production of virions by stable packaging lines for use in transducing of human HSCs for the purpose of gene therapy.

REFERENCES

1. Bank, A., Markowitz, D. G., and Goff, S. P. U.S. Pat. No. 6,372,502.
2. Burns J., Friedmann T., Driever W., Burrascano M., and Yee J. (1993) Vesiticular stomatitius virus G glycoprotein pseudotyped retroviral vectors: Concentration to very high titers and efficient gene expression in mammalian and non-mammalian cells. Proc. Natl. Acad. Sci. USA 90:8033–8037.
3. Cone, R. D. and Mulligan, R. C. (1984) High-efficiency gene transfer into mammalian cells: generation of helper-free recombinant retrovirus with broad mammalian host range. Proc. Natl. Acad. Sci. USA 81:6349–6353.
4. Cosset F. L., Takeuchi Y., Battini J. L., Weiss R. A., and Collins M. K. (1995) High-titer packaging cells producing recombinant retroviruses resistant to human serum. J. Virology 69:7430–7436.
5. Gatlin J., Melkus M., Padgett A., Kelly P., and Garcia J. (2001) Engraftment of NOD/SCID Mice with human CD34+ Cells transduced by concentrated oncoretroviral vector particles pseudotyped with the feline endogenous retrovirus (RD114) Envelope Protein. J. Virology 75:9995–9999.
6. Gerin, P. A., Gilligan, M. G., Searle, P. F., and Al-Rubeai, M. (1999) Improved titers of retroviral vectors from the human FLYRD18 packaging cell line in serum and protein-free medium. Human Gene Ther. 10:1965–1974.
7. Kaubisch A., Ward M., Schoetz S., Hesdorffer C., and Bank A. (1999) Up-regulation of amphotrophic retroviral receptor expression in human peripheral blood CD34+ cells. Am. J. Hematol. 61:243–253.
8. Kavanaugh M. P., Miller D. G., Zhang W., Law W., Kozak S. L., Kabat D., and Miller A. D. (1994) Cell-surface receptors for gibbon ape leukemia virus and amphotropic murine retrovirus are inducible sodium-dependent phosphate transporters. Proc. Natl. Acad. Sci. USA 91:7071–7075.
9. Kelly, P. F., Vandergriff, J., Nathwani, A., Nienhuis, A. W. and Vanin, E. F. (2000) Highly efficient gene transfer into cord blood nonobese diabetic/severe combined immunodeficiency repopulating cells by oncoretroviral vector particles pseudotyped with the feline endogenous retrovirus (RD114) envelope protein. Blood 96:1206–1214.
10. Markowitz, D. G., and Bank, A. (1988a) A safe packaging line for gene transfer: separating viral genes on two different plasmids. J. Virology 62:1120–1124.
11. Markowitz D., Goff S., and Bank A. (1988b) Construction and use of a safe and efficient amphotropic packaging cell line. Virology 167:400–405.

12. Miller, A. D. and Buttimore, C. (1986) Redesign of retrovirus packaging cell lines to avoid recombination leading to helper virus production. Mol. Cell. Biol. 6:2895–2902.
13. Orlic D., Girard L. J., Jordan C. T., Anderson S. M., Cline A. P., and Bodine D. M. (1996) The level of mRNA encoding the amphotropic retrovirus receptor in mouse and human hematopoietic stem cells is low and correlates with the efficiency of retrovirus transduction. Proc. Natl. Acad. Sci. USA 93:11097–11102.
14. Pensiero, M. N., Wysocki, C. A., Nader, K., and Kikuchi, G. E. (1996) Development of amphotropic murine retrovirus vectors resistant to inactivation by human serum. Human Gene Ther. 7:1095–1101.
15. Porter C. D., Collins M. K. L., Tailor S. C., Parkar M. H., Cosset F. L., Weiss R. A., and Takeuchi Y. (1996) Comparison of efficiency of infection of human gene therapy target cells via four different retroviral receptors. Human Gene Ther. 7:913–919.
16. Raftopoulos H., Ward M., Leboulch P., and Bank A. (1997) Long-term transfer and expression of a human β-globin gene in a mouse transplant model. Blood 90:3414–3422.
17. Sorge, J., Wright, D., Erdman, V. D. and Cutting A. E. (1984) Amphotropic retrovirus vector system for human cell gene transfer. Mol. Cell. Biol. 4:1730–1737.
18. Takeuchi, Y., Cosset, F. L., Lachmann, P. J., Okada, H., Weiss, R. A., and Collins, M. K. (1994) Type C retrovirus inactivation by human complement is determined by both the viral genome and the producer cell. J. Virology 68:8001–8007.
19. Ward M., Richardson C., Pioli P., Smith L., Podda S., Goff S., Hesdorffer C., and Bank A. (1994) Transfer and expression of the human multiple drug resistance gene in human CD34+ cells. Blood 84:1408–1414.
20. Ward M., Richardson C., Pioli P., Urzi G., Ayello J., Reiss R., Hesdorffer C., and Bank A. (1996) Transfer and expression of the human MDR gene in peripheral blood progenitor cells. Clin. Cancer Res. 2:873–876.

What is claimed is:

1. The retroviral packaging cell designated RDF 21 (ATCC Patent Deposit Designation PTA-4440).

2. A method for producing a retroviral producer cell comprising transducing the retroviral packaging cell of claim 1 with a retroviral vector comprising a nucleic acid sequence of interest so as to cause the cell to secrete virions comprising the nucleic acid sequence of interest, thereby producing a retroviral producer cell.

3. The method of claim 2, wherein the nucleic acid of interest comprises a therapeutic gene.

4. The method of claim 3, wherein the nucleic acid of interest further comprises a selectable marker.

5. The retroviral producer cell produced by the method of claim 2.

6. A method for producing retroviral supernatant comprising culturing the retroviral producer cell of claim 5 under suitable conditions, thereby producing retroviral supernatant.

7. The method of claim 6, further comprising the steps of collecting and concentrating the retroviral supernatant.

8. A kit comprising the retroviral packaging cell of claim 1, and instructions for use.

9. A kit comprising the retroviral packaging cell of claim 1, and a retroviral vector comprising a nucleic acid of interest.

10. The kit of claim 9, further comprising instructions for use.

* * * * *